US00RE37767E

(19) United States
(12) Reissued Patent
Fleer et al.

(10) Patent Number: US RE37,767 E
(45) Date of Reissued Patent: Jun. 25, 2002

(54) HIGHLY STABLE RECOMBINANT YEASTS FOR THE PRODUCTION OF RECOMBINANT PROTEINS

(75) Inventors: Reinhard Fleer, Orsay; Alain Fournier, Chatenay-Malabry; Patrice Yeh, Gif sur Yvette, all of (FR)

(73) Assignee: Aventis Pharma S.A., Antony Cedex (FR)

(21) Appl. No.: 09/640,304

(22) PCT Filed: Aug. 3, 1992

(86) PCT No.: PCT/FR92/00769

§ 371 (c)(1), (2), (4) Date: May 20, 1994

(87) PCT Pub. No.: WO93/03159

PCT Pub. Date: Feb. 18, 1993

Related U.S. Patent Documents

Reissue of:
(64) Patent No.: 5,593,858
Issued: Jan. 14, 1997
Appl. No.: 08/190,103
Filed: May 20, 1994

(30) Foreign Application Priority Data

Aug. 2, 1991 (FR) ..... 91 09854

(51) Int. Cl.[7] ..... C12P 21/02; C12N 1/15; C12N 15/81

(52) U.S. Cl. ..... 435/69.1; 435/69.3; 435/69.4; 435/69.51; 435/69.52; 435/69.6; 435/183; 435/254.2; 435/254.21; 435/255; 435/320.1; 435/440

(58) Field of Search ..... 435/254.2, 254.21, 435/320.1, 440, 255, 69.1, 69.4, 69.3, 69.6, 69.51, 69.52, 183

(56) References Cited

U.S. PATENT DOCUMENTS 4,857,467 A * 8/1989 Sreekrishna et al.

FOREIGN PATENT DOCUMENTS

EP 0 361 991 * 4/1990

OTHER PUBLICATIONS

Fournier et al., "The primary structure of the 3–phosphoglycerate kinase (PGK) gene from *Kluyveromyces lactis,*" Nuc. Acids Rec. vol. 18, p. 365 (1990).
Goffrini et al., "RAG1 Gene of the Year *Kluyveromyces lactis* Codes for a Sugar Transporter," Nucleic Acids Res. vol. 18, No. 7, p. 5294 (1990).
Ohya et al., "Structure–based systematic isolation of conditional–lethal mutations in the single yeast calmodulin gene," Genetics vol. 138, pp. 1041–1054 (1994).
Rothstein et al., "One–step gene disruption in yeast," Methods in Enzymology vol. 101, pp. 202–211 (1983).

* cited by examiner

*Primary Examiner*—James Ketter
(74) *Attorney, Agent, or Firm*—Finnegan, Henderson, Farabow, Garrett & Dunner, L.L.P.

(57) ABSTRACT

Novel recombinant yeasts are disclosed which are highly stable in a complex medium. Said yeasts are of the Kluyveromyces genus in which an essential gene is nonfunctional, containing a vector bearing a functional copy of said gene.

27 Claims, 13 Drawing Sheets

OLIGODEOXYNUCLEOTIDES

ADAPTOR 1

(SEQ ID NO: 1) A 5' CGTCGACACGCGTGCGCGCCCGCGGCCAATGGGGCCC 3'

(SEQ ID NO: 2) B 5' TCGAGGGCCCCATTGGCCGCGGGCGCGCACGCGTGTCGACGAGCT 3'

ADAPTOR 2

(SEQ ID NO: 3) C 5' AATTAGGCCAATGGGGCCGACGTCGCATGCGGCGCCGAGCT 3'

(SEQ ID NO: 4) D 5' CGGCGCCGCATGCGACGTCGGCCCCATTGGCCT 3'

ADAPTOR 3

(SEQ ID NO: 5) E 5' AATTCCCCGCGCGCCCATCGATCCGCTAGCCCACGCGTCCA 3'

(SEQ ID NO: 6) F 5' GATCTGGACGCGTGGGCTAGCGGATCGATGGGCGCGCGGGG 3'

PCR (SEQ ID NO: 7) G 5' TGCCTTCGGTACCGCTCAC 3'

(SEQ ID NO: 8) H 5' AGAAGGGAAGGGATGATGGA 3'

FIG. 4

Figure 1:
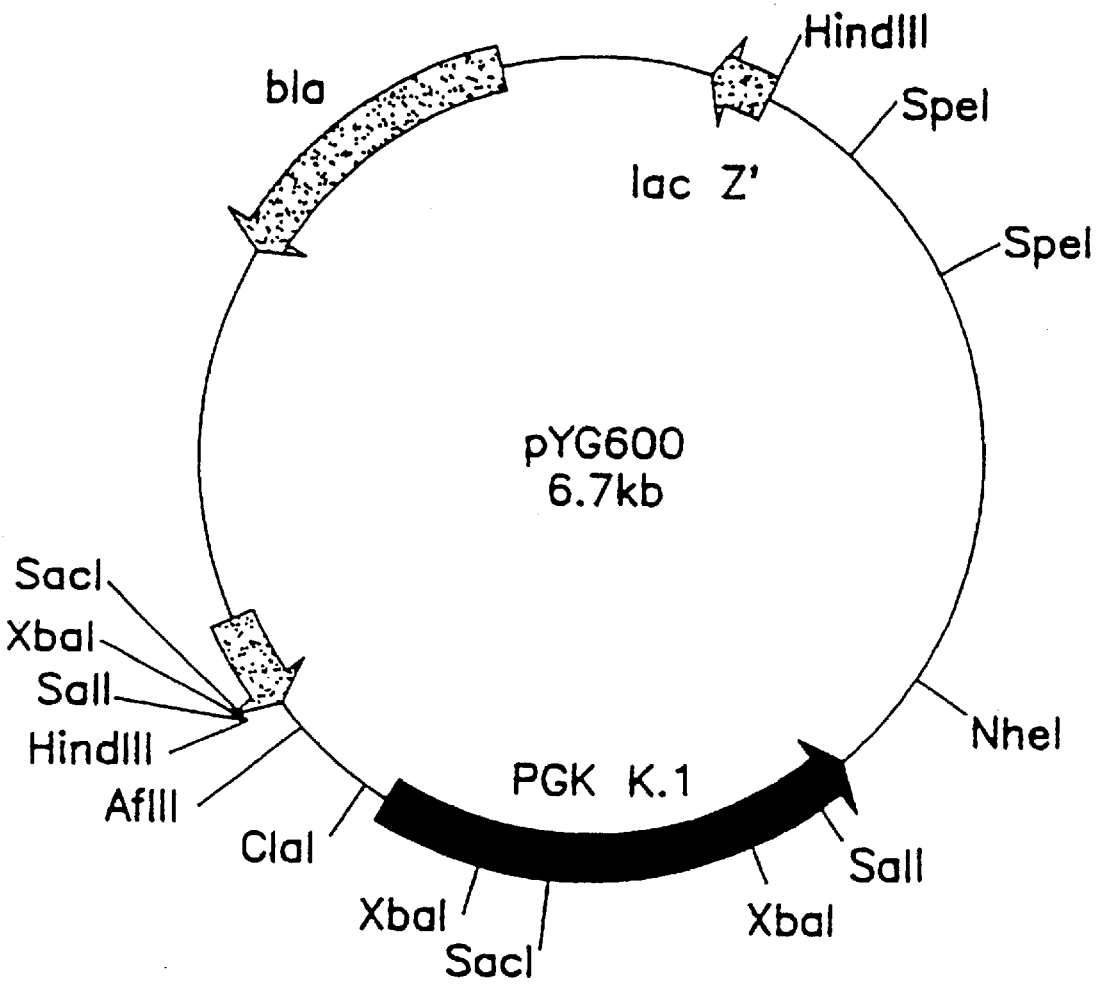

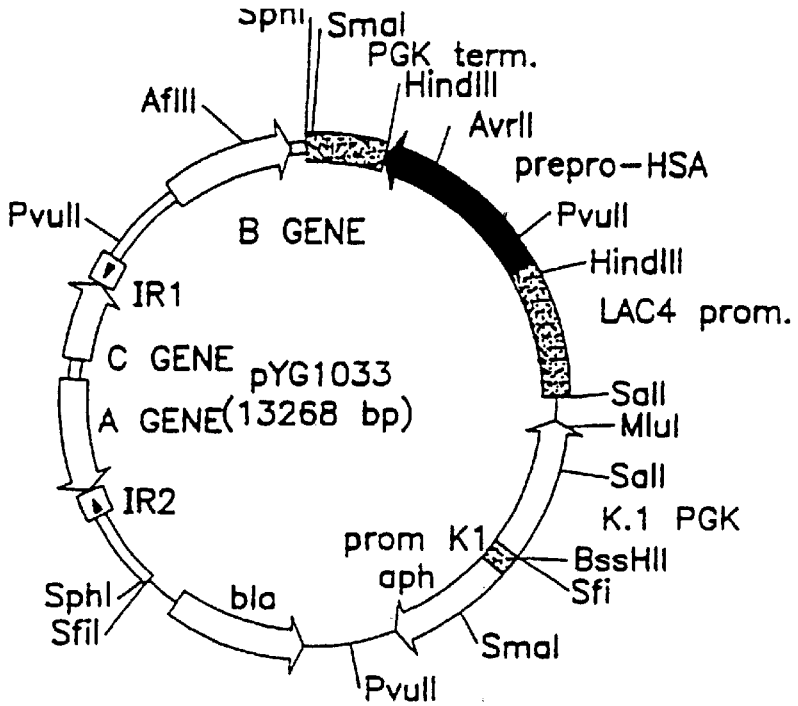
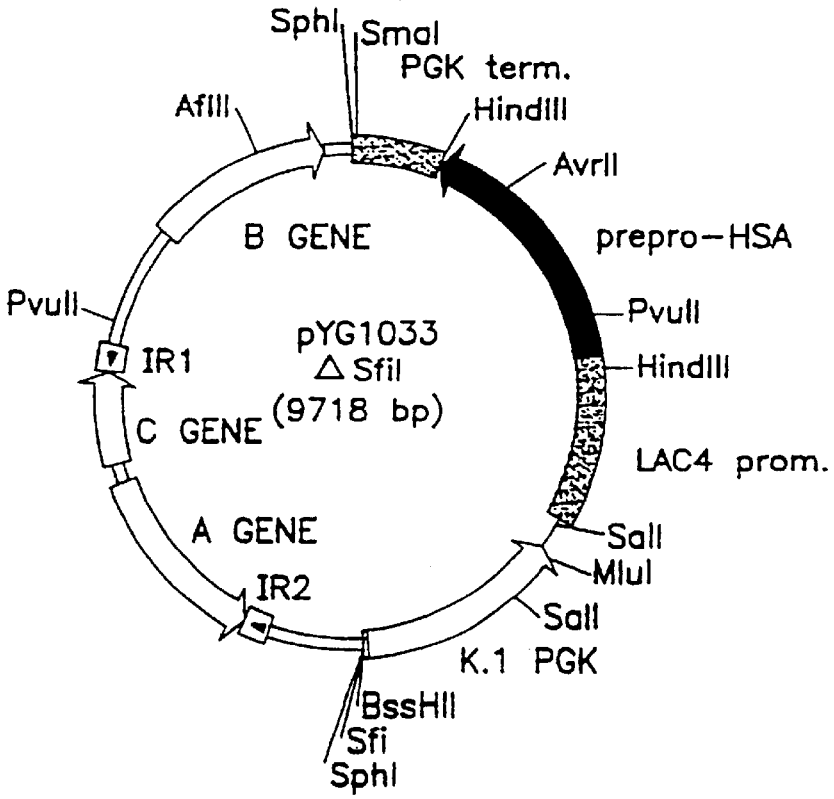
FIG. 9

HIGHLY STABLE RECOMBINANT YEASTS FOR THE PRODUCTION OF RECOMBINANT PROTEINS

Matter enclosed in heavy brackets [ ] appears in the original patent but forms no part of this reissue specification; matter printed in italics indicates the additions made by reissue.

The present invention relates to the field of biotechnology, and more particularly to that of industrial fermentations by recombinant microorganisms.

Still more particularly, it relates to a host/vector pair which is highly stable in a complex medium, its preparation and its use in industrial fermentation.

The advances accomplished in the field of molecular biology have made it possible to modify microorganisms in order to make them produce specific recombinant proteins, preferably heterologous proteins. In particular, numerous genetic studies have been performed on the bacterium E. coli. More recently, yeasts such as Saccharomyces, Kluyveromyces, Pichia, or even Hansenula, have emerged as promising host organisms for this mode of protein production.

However, the industrial application of these new modes of production is still limited, especially by the problems of the efficacy of gene expression in these recombinant microorganisms, and by the difficulty of obtaining recombinant cells which are stable under industrial fermentation conditions. One of the essential operational constraints is indeed linked to the segregational stability of an expression vector inside the host used. At the industrial level, a vector should possess a high stability over at least 25 successive generations, which approximately represent the number of generations required to go as far as the end of a 200-$m^3$ fed batch-type industrial fermenter (Principles of Fermentation Technology, Stanburry and Whitaker, Pergamon Press, Oxford, 1984). The stability of the vector must be even higher in the case of continuous fermentation where it must reach not less than about one hundred generations.

In bacteria, the most common solution used in the laboratory consists of inserting a gene for resistance to an antibiotic into the plasmid used, which endows the bacteria with the capacity to survive and grow in a selective medium containing said antibiotic. However, because of security and regulatory constraints in the field of biotechnology, it is essential to be able to avoid the use of antibiotic resistance genes at the industrial level. In yeasts, the most commonly used method consists of culturing cells with a defective pathway for the biosynthesis of amino acids (Trp, Leu, His) or of purine (adenine) or pyrimidine (uracil) bases, said cells being transformed by a vector containing a gene which is capable of complementing this defect. However, this approach requires the use of media lacking the amino acid or the base for which the host strain is auxotrophic. The use of such synthetic media has numerous disadvantages. In particular, these media are expensive, which is incompatible with an industrial use, and furthermore, they lead to slower growth of the cells and to a smaller biomass.

A solution has been proposed to avoid the use of a synthetic medium or of antibiotic resistance genes, which consists of (i) mutating a gene which is essential for survival in a complex medium in the host cell and (ii) introducing an intact copy of said gene into the expansion plasmid used. This system, the principle of which is to force the host cell to retain its plasmid, has enabled the stability of the host/vector pair to be increased. This system has, in particular, been described for E. coli, for the dapD gene which encodes tetrahydropicolinate-N-succinyl transferase (EP 258 118), for the va1S gene whose product is an enzyme which is required for protein synthesis (Skogman and Nilsson, Gene 31 (1984) 117), and for the ssb gene whose product is essential for DNA replication and for the survival of the cell (Porter et al., Bio/technology vol. 8 (1990) 47). Ferrari et al. have also described the use of the racemase alanine gene for stabilising a plasmid inside a B. subtilis mutant in which this gene was not functional (Bio/technology vol. 3 (1985) 1003). Application WO 86/01224 describes a similar selection system which is suitable for the yeast S. cerevisiae. This system uses the yeast S. cerevisiae which has a mutation in 2 genes which are involved in the biosynthesis of uracil. It consists of (i) inactivating one of the genes for the synthesis of uracil, (ii) transforming said cell with a vector carrying the active gene, and (iii) blocking the other metabolic pathway by mutagenesis.

Another approach for obtaining expression systems which are stable in complex media consists of using vectors which are integrated into the genome of the host cell. However, this system enables only a small number of copies of the vector to be obtained per recombinant cell, and furthermore, the transformation frequency is low. Under these conditions, the levels of expression of heterologous genes are not always satisfactory. A method enabling amplification of a gene which is integrated into the genome has, moreover, been developed in S. cerevisiae, by directing integration towards the genes encoding ribosomal proteins, said genes being present in multiple copies in the genome. However, this system proves to be unstable when the integrated genes are expressed at high levels, whether they are homologous or heterologous genes.

Currently, the use of the new yeasts, different from S. cerevisiae, for the production of recombinant proteins requires the development of tools which are adapted to these microorganisms, in order to resolve in particular the problems of stability of expression vectors for heterologous genes. More specifically, yeasts which are taxonomically related to the Kluyveromyces genus appear to possess a particularly advantageous capacity for secreting recombinant proteins. This has been observed in particular in the case of the yeast K. lactis, for the production of chymosin (EP 96430), IL-1β or human serum albumin (EP 361991). However, no sufficiently stable multicopy expression vectors exist in this organism to permit its use in industrial processes. In particular, no vectors exist which are stable in complex media, enabling large-scale processes, especially continuous processes, to be envisaged using this organism. Indeed, although certain vectors which are stable in K. lactis have been described (EP 361991), the introduction of a heterologous gene expression cassette into these vectors produces a substantial destabilising effect, especially under conditions for inducing production.

A particularly efficient means for stabilising host/vector pairs in which the host is a yeast of the Kluyveromyces genus, has now been found.

One embodiment of the invention consists of a host/vector pair which is highly stable in a complex medium, characterised in that the host is a yeast of the Kluyveromyces genus in which a gene which is essential for its growth in said medium is nonfunctional, and in that the vector carries a functional copy of said gene.

Within the context of the present invention, complex medium is understood to mean any medium for industrial fermentation which is compatible with the economic constraints of a large-scale operation. In particular, it relates to media containing industrial-type raw materials: maize soluble extract, yeast extract, molasses or "distillers", for example, as opposed to defined synthetic media which are supplemented (for example with antibiotics). However, it is understood that the present invention may also be used on synthetic media, although this embodiment is less advantageous.

Moreover, it is understood that the functional gene which is present in the vector may be a homologous or heterologous gene.

Genes which are essential for the growth of the host cell in a complex medium include genes which are involved in the metabolism of a carbon source present in the medium (galactose, lactose, glucose and the like), and genes participating in cellular division, in membrane synthesis, in protein synthesis or DNA replication or transcription.

More preferably, the invention consists of a host/vector pair which is highly stable in a complex medium, characterised in that the host is a yeast of the Kluyveromyces genus in which a gene which is involved in glycolysis is nonfunctional, and in that the vector carries a functional copy of said gene.

It has indeed been shown that host/vector pairs which are very stable in a complex medium, which is compatible with an industrial operation, may be obtained in Kluyveromyces by rendering the host cell dependent on its plasmid when it has to call into play a glycolysis step in order to metabolise the carbon sources of the medium.

More preferably, the present invention relates to host/vector pairs in which the host is chosen from the yeasts Kluyveromyces lactis and Kluyveromyces fragilis.

In yeasts, glycolysis involves a succession of complex enzymatic and chemical steps leading to the formation of molecules of ATP and ethanol. The main enzymes involved in this pathway are known and some of the genes encoding these enzymes have been identified and cloned: the genes encoding phosphofructokinase (Kopperschlager et al., Eur. J. Biochem. 81 (1977) 317); pyruvate kinase (Aust et al., J. Biol. Chem. 253 (1978) 7508); phosphoglycerate kinase (Scopes, Meth. Enzymol. 42 (1975) 134); phosphoglycerate mutase (Price et al., FEBS Letters 143 (1982) 283); triose phosphate isomerase (Alber et al., J. Biol. Chem. 256 (1981) 1356); pyruvate decarboxylase (Gounarb et al., Biochim. Biophys. Acta 405 (1975) 492), and phosphoglucose isomerase (Noltmann, The enzymes, vol VI, Academic Press, N.Y., 271, 1972) have been identified in S. cerevisiae. Some glycolytic genes have been cloned into K. lactis. They are, more specifically, the RAG1 and RAG2 genes which encode a sugar-transporting protein (Goffrini et al., Nucl. Acid. Res. 18 (1990) 5294) and a phosphoglucose isomerase (Wésolowski-Louvel, Nucl. Acid. Res. 16 (1988) 8714), respectively; and genes which encode alcohol dehydrogenases, ADH (Saliola et al., Yeast 6 (1990) 193–204; Saliola et al., Yeast 7 (1991) 391–400).

However, these genes cannot be efficiently used for stabilising expression vectors in yeasts of the Kluyveromyces genus. Indeed, the RAG1 gene and ADH genes are not essential for the use of glucose. Furthermore, earlier work on Kluyveromyces has shown that the RAG2 gene, whose PGI equivalent is known to be essential for the growth of the yeast S. cerevisiae on a glucose-containing medium, was not essential in Kluyveromyces (Wésolowski-Louvel, as mentioned above; Goffrini et al., Yeast 5 (1989) 99–106). This result indicated a difference in behaviour for the Kluyveromyces and Saccharomyces yeasts with respect to the use of glucose, which did not enable the production, in Kluyveromyces, of a stable host/vector pair by using glycolytic genes as selection markers.

Under these conditions, the use of these genes for the stabilisation of expression vectors in yeasts of the Kluyveromyces genus was neither described nor suggested, nor possible.

Surprisingly, the applicant has now shown that some glycolytic genes may be essential for the growth and/or survival of yeasts of the Kluyveromyces genus in a complex medium and that they may enable the production of particularly stable host/vector pairs. In particular, stable and efficient systems may be obtained when the glycolytic gene chosen is a single gene whose product is essential for the metabolism of the carbon sources of the medium by this yeast. Indeed, some glycolysis steps involve activities which may be encoded by several genes. This is the case, especially in S. cerevisiae, for enolase (ENO), phosphofructokinase (PFK), glyceraldehyde-3-phosphate dehydrogenase (GAPDH) or alcohol dehydrogenase (ADH) activities which are encoded by several genes. In this case, inactivation of one of these enzymatic activities would require the inactivation of all the genes which are capable of encoding it.

Preferably, in the host/vector pair of the invention, the gene involved in glycolysis is a single gene whose product is essential for the metabolism of the carbon sources of the medium by the yeast.

Still more preferably, it is a gene which is chosen from the genes encoding phosphoglycerate kinase (PGK), phosoglycerate mutase (GPM), pyruvate kinase (PYK) and triose phosphate isomerase (TPI).

The selected gene may be rendered nonfunctional in the host yeast in various ways. It is possible to use nonspecific mutagenesis techniques. The yeasts may be treated with physical agents (X rays; ultra violet rays and the like) or chemical agents (intercalating agents, mono- or bialkylating agents and the like). The yeasts thus treated are then selected on various media depending on the desired mutation.

It is also possible to use specific mutagenesis tools, especially techniques for mutational insertions into DNA or for gene replacement by homologous recombination (Rothstein, Meth. Enzymol. 101 (1983) 202). To this effect, at least 2 mutagenesis pathways are possible:

- replacing the gene to be deleted by a dominant selection marker of the antibiotic resistance marker type (geneticin, fluomycin and the like). It has been possible to apply this strategy directly to a wild strain;
- replacing the gene to be deleted by an intact copy of a gene complementing an auxotrophy (ura3, trp1, leu2, and the like) of the strain used. This strategy may be applied to any strain exhibiting an auxotrophy, or to a wild strain previously made auxotrophic.

Preferably, in the host/vector pair of the invention, the functional copy of the essential gene present in the vector is placed under the control of a weal promoter. This advantageous embodiment enhances the stability of the pair and the increase in the number of copies of the vector per host cell and, consequently, tends to increase the level of expression of a recombinant gene. Examples of weak promoters which may be used for this purpose include the bidirectional promoter of the killer toxin gene (Tanguy-Rougeau et al., Gene 91 (1990) 43) or that of a heterologous gene such as the promoter of the acid phosphatase gene of S. cerevisiae under repression conditions (phosphate-containing culture medium). In another preferred embodiment of the invention, the functional copy of the essential gene which is present in the vector is either completely free of promoter or is placed under the control of a defective promoter, whether as a result of a mutation of the promoter itself or as a result of the inactivation of a gene involved in the transcriptional activation of said promoter. In another embodiment of the invention, the essential gene present in the vector may be a gene which is defective under certain conditions such as temperature conditions, for example. In particular, it may be a heat-sensitive gene.

Preferably, in the host/vector pair of the invention, the vector comprises, in addition, a DNA sequence containing a structural gene encoding at least a desired protein, and signals permitting its expression.

In a preferred embodiment of the invention, the structural gene encodes a protein which is important in the pharmaceutical or agri-foodstuffs industries.

Structural genes include, but are not limited to, enzymes (such as, in particular, superoxide dismutase, catalase, amylases, lipases, amidases, chymosin and the like), blood derivatives (such as serum albumin or variants or precursors thereof, alpha- or beta-globin, factor VIII, factor IX, the von Willebrand factor or portions thereof, fibronectin, alpha-1-antitrypsin and the like), insulin and its variants, lymphokines [such as interleukins, interferons, colony stimulating factors (G-CSF, GM-CSF, M-CSF and the like), TNF, TRF, MIP and the like], growth factors (such as growth hormone, erythropoietin, FGF, EGF, PDGF, TGF and the like), apolipoproteins, antigenic polypeptides for the production of vaccines (hepatitis, cytomegalovirus, Epstein-Barr, herpes and the like), viral receptors, or even fusions of polypeptides such as in particular fusions containing an active portion fused with a stabilising portion (for example, fusions between albumin or fragments of albumin and the receptor or a portion of a virus receptor (CD4 and the like)).

Advantageously, moreover, the DNA sequence comprises, in addition, signals enabling the secretion of the recombinant protein. These signals may correspond to the natural signals for the secretion of the protein in question, but they may also be of a heterologous origin. In particular, secretion signals derived from yeast genes such as those from the killer toxin or alpha pheromone gene may be used.

Preferably, the structural gene encodes human serum albumin, its precursors or its molecular variants. "Molecular variants" of albumin is understood to mean the natural variants resulting from the polymorphism of albumin, the structural derivatives possessing an albumin-type activity, the truncated forms of albumin, or any albumin-based hybrid protein.

In another embodiment, the structural gene(s) encodes(s) polypeptides which are involved at the genetic or biochemical level in the biosynthesis of a metabolite. In particular, they may be genes which are involved in the biosynthesis of amino acids, antibiotics or vitamins.

Generally, the signals enabling the expression of the structural gene are chosen from transcription promoters and terminators. It is understood that these signals are chosen as a function of the structural gene and of the desired result. In particular, it may be preferable to use in certain cases a promoter which can be regulated so as to be able to uncouple the host growth phase(s) from the gene expression phase. Likewise, for reasons related to strength and compatibility, it may be preferable to use, in certain cases, the natural promoters for the structural genes and, in other cases, promoters of a different origin.

Preferably, the promoters used are derived from yeast genes and, still more preferably, from yeast glycolytic genes. The promoters derived from the glycolytic genes of yeasts of the Saccharomyces or Kluyveromyces genus are of very particular importance. In particular, examples include the promoters of genes which encode phosphoglycerate kinase (PGK), glyceraldehyde-3-phosphate dehydrogenase (GPD), enolases (ENO) or alcohol dehydrogenases (ADH). Promoters derived from genes which are strongly expressed, such as the lactase gene (LAC4), acid phosphatase gene (PHO5) or gene for elongation factors (TEF) may also be mentioned.

Moreover, these promoter regions may be modified by mutagenesis, for example, so as to add additional elements for the control of transcription, such as in particular UAS regions ("Upstream Activating Sequence"). By way of example, a hybrid promoter between the promoters of the PGK and GAL1/GAL10 genes of S. cerevisiae gives good results.

The host/vector pairs of the invention may be used in methods for producing recombinant proteins. They thus enable particularly efficient production systems to be achieved in yeasts of the Kluyveromyces genus.

In this respect, another embodiment of the invention relates to a method for producing a recombinant protein in which a host/vector pair as defined above, comprising the structural gene which encodes said protein under the control of signals permitting its expression, is cultured and the protein produced is recovered.

Such a method enables the production of proteins which are important in the pharmaceutical or agri-foodstuffs industries, such as those stated above. It is particularly suitable for the production of human serum albumin, its precursors and molecular variants, although not limited thereto.

The host/vector pairs of the invention may also be used directly as catalysts in bioconversion reactions.

Another subject of the invention relates to the expression vectors for yeasts of the Kluyveromyces genus carrying a functional copy of a gene which is essential for the growth of the Kluyveromyces yeast on a complex medium.

More preferably, the essential gene is a gene which is involved in one of the above-mentioned functions. This gene may be obtained by any method known to a person skilled in the art (hybridisation cloning using heterologous probes, mutant complementation cloning, and the like).

Advantageously, the vectors of the invention are free of any bacterial sequences. It has indeed been shown that it is possible to transform Kluyveromyces yeasts with such vectors in vitro. This system has the advantage of enabling the use of vectors which are smaller and therefore easier to manipulate and capable of accepting larger recombinant DNA sequences.

Examples of such vectors include, in particular, the vectors pYG1023, pYG1033 and pYG1033ΔSfiI, which are described in the examples.

Compared with the prior art systems, some of the advantages of the present invention are:

- the very efficient stabilisation of plasmids in yeasts of the Kluyveromyces genus;
- the possibility of culturing the recombinant cells in a medium which is not very expensive and which can be easily obtained in large amounts; and
- the possibility of detecting recombinant cells in a very simple manner, which renders the use of additional selection markers unnecessary. Indeed, it is generally necessary to use one or more markers in order to identify and/or select recombinant cells. Genes which confer resistance to antibiotics such as in particular geneticin (aph gene), or to other compounds which are toxic for the cell, such as copper ions (CUP gene), are most often involved. Genes complementing auxotrophies of the host cell (URA3, TRP1, or LEU2 genes and the like) may also be involved. The host/vector pairs of the invention make it possible to avoid the use of any other selection marker.

The present invention will be more completely described by means of the following examples which should be considered as illustrative and nonlimiting.

LEGEND TO THE FIGURES

FIG. 1: Restriction map of the plasmid pYG600. bla=β-lactamase gene which confers resistance to ampicillin.

Figure 2:
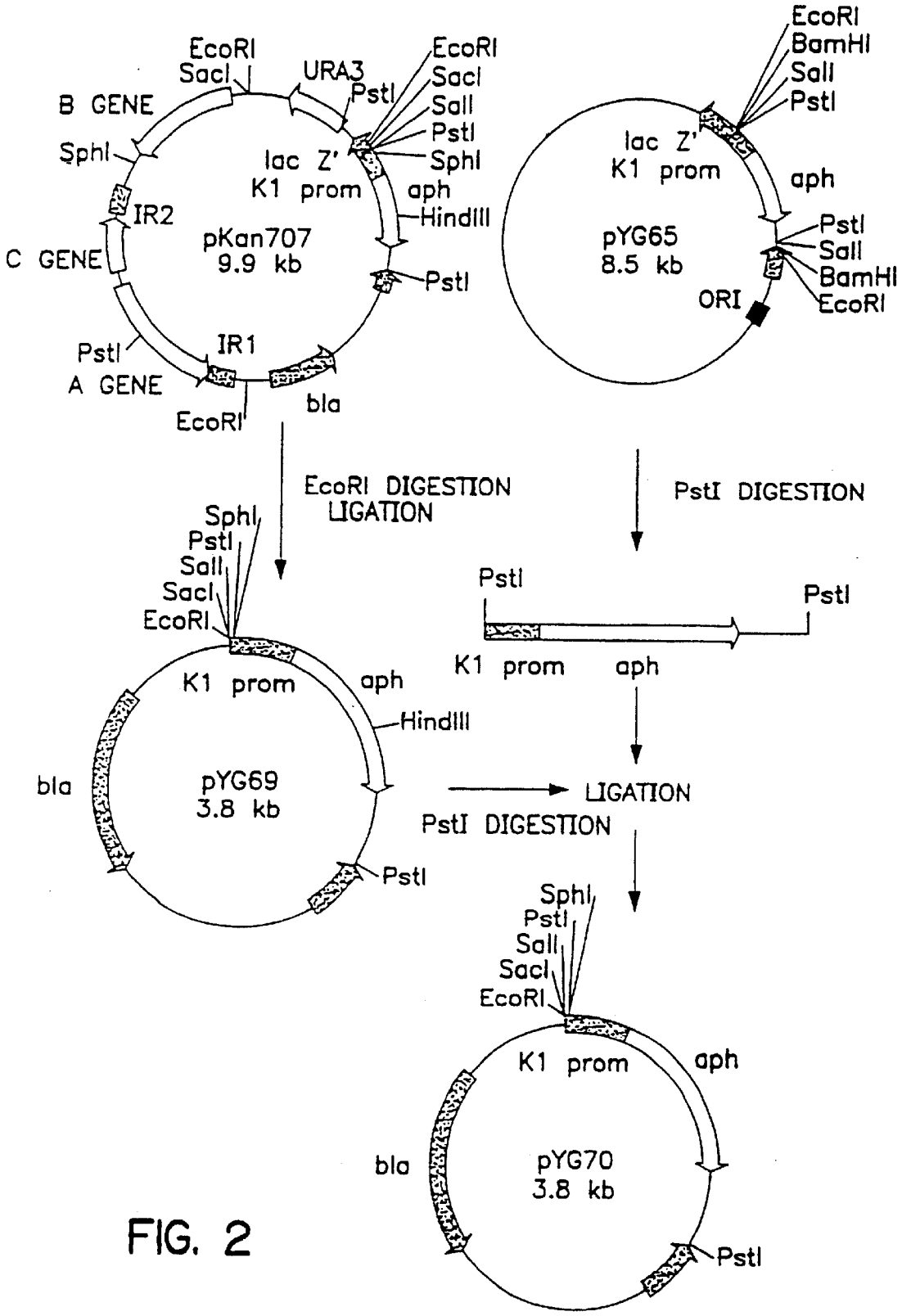

FIG. 2: Strategy for constructing the plasmid pYG70. aph=3'-aminoglycoside phosphotransferase gene which confers resistance to geneticin (G418); prom=promoter; IR=inverted repeat sequence; ORI=origin of replication; LacZ'=β-galactosidase structural gene.

Figure 3:
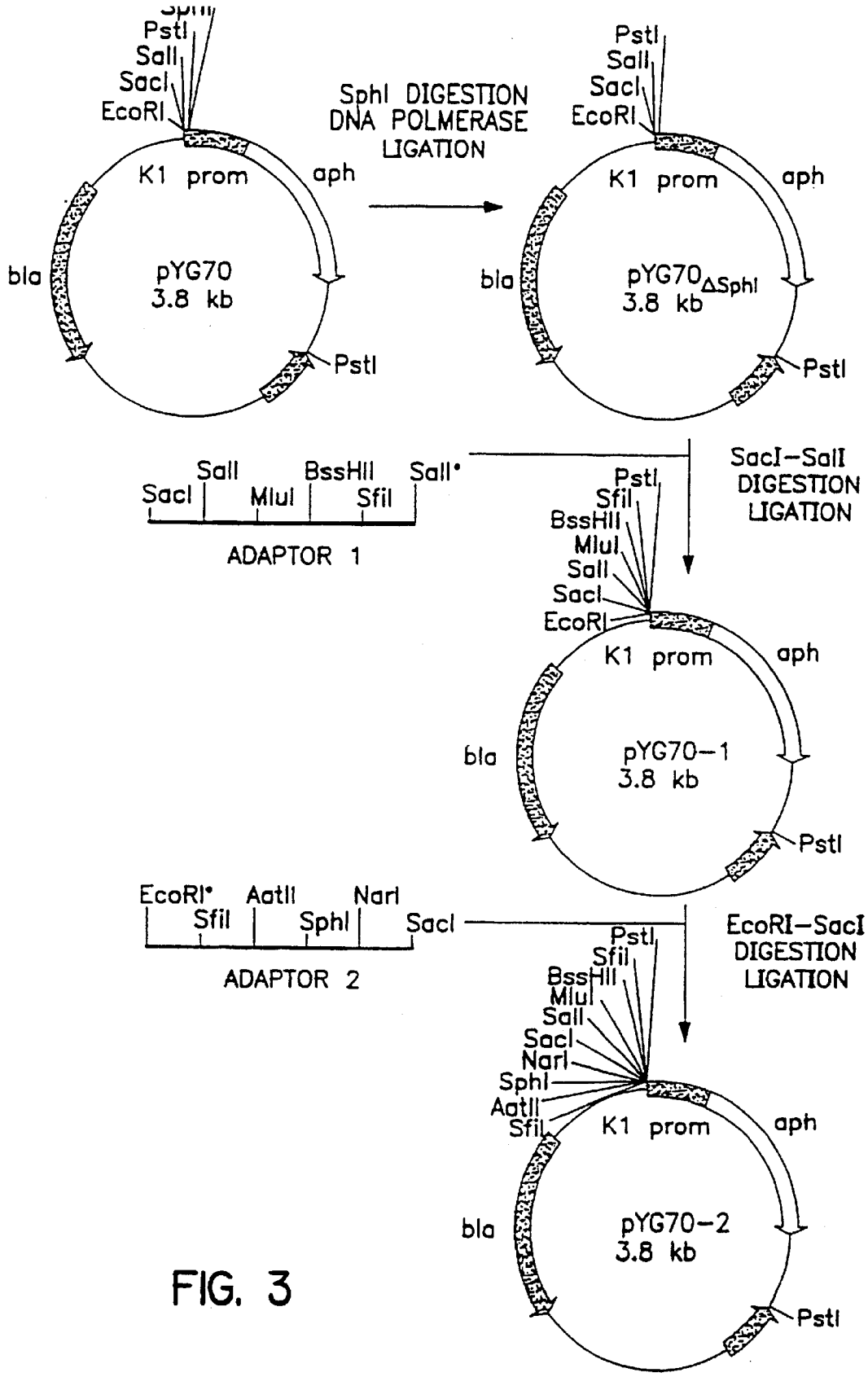

FIG. 3: Strategy for constructing the plasmid pYG70-2. See FIG. 2 for the legend. The sites marked with an (*) possess ends which are co mpatible with the corresponding sites without restoring, after ligation, cleavage sites recognised by said enzymes.

FIG. 4: Sequence of synthetic oligonucleotides A-H (SEQ ID NOS: 1–8) which were used in constructing the adaptors 1 to 3 and in the PCR reaction for checking the genotype of the pgk mutants (Example 3.2.(ii)).

Figure 5:
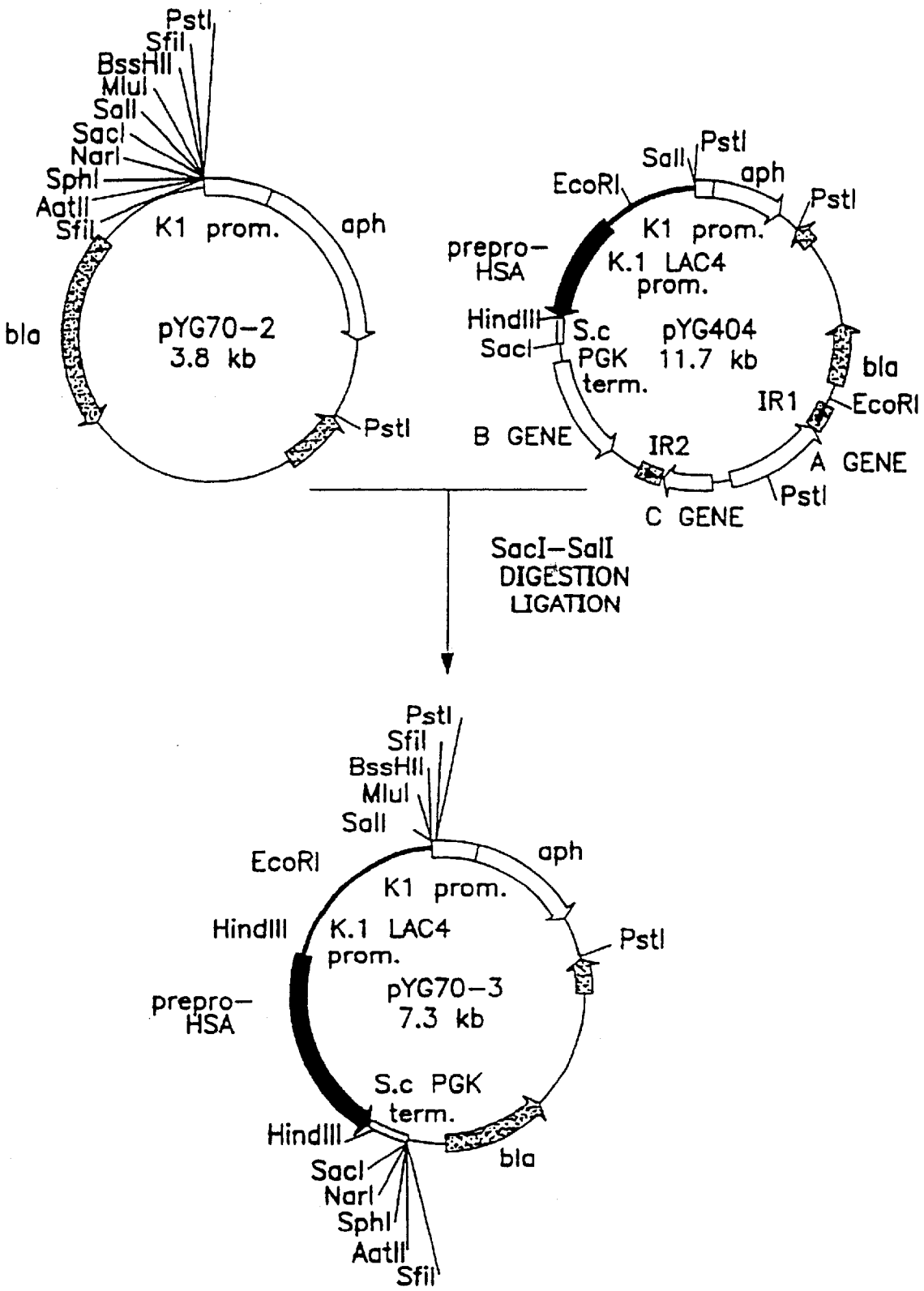

FIG. 5: Strategy for constructing the plasmid pYG70-3. See FIG. 2 for the legend. term=terminator.

Figure 6:
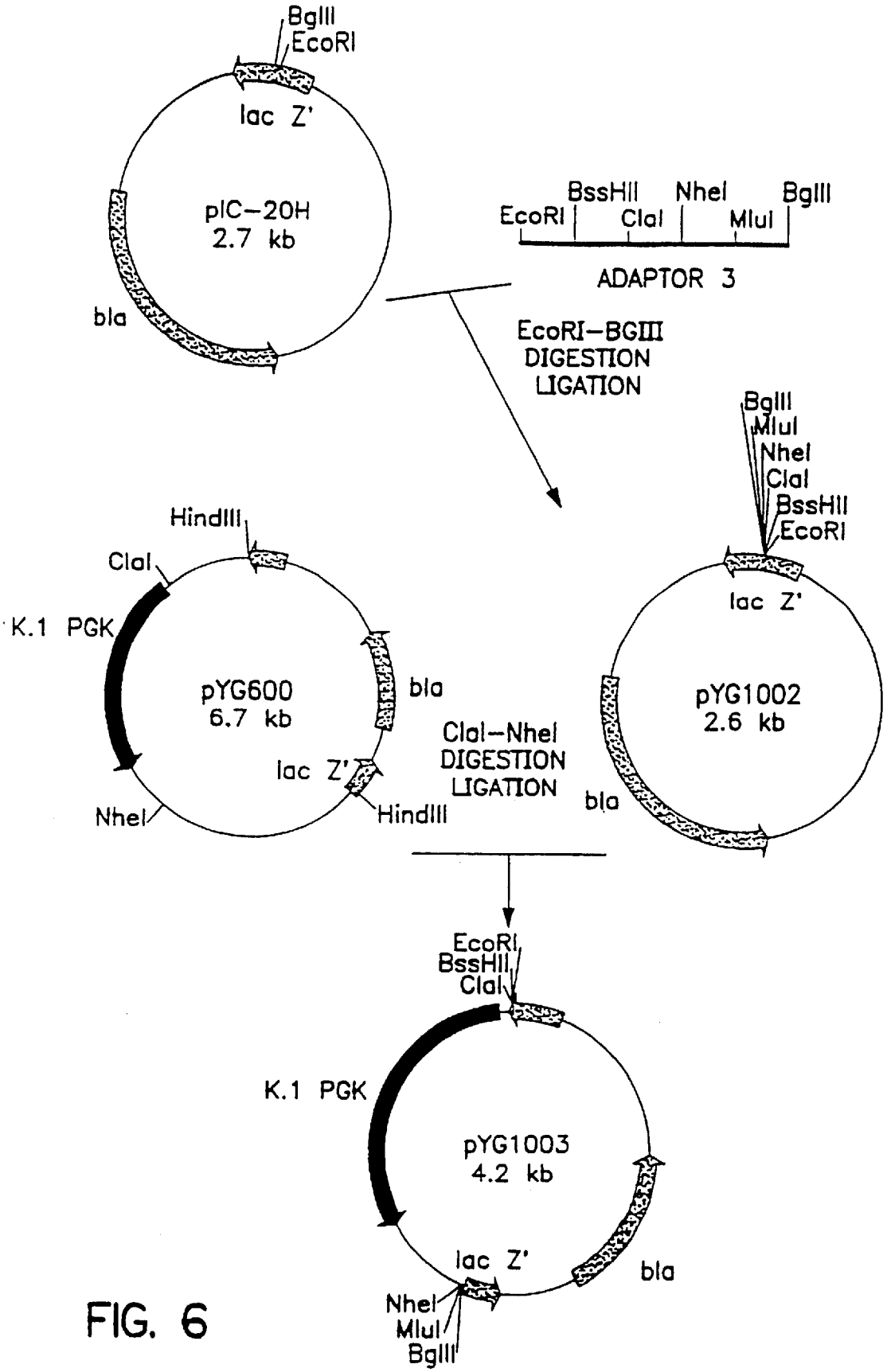

FIG. 6: Strategy for constructing the plasmid pYG1003. See FIG. 2 for the legend.

Figure 7:
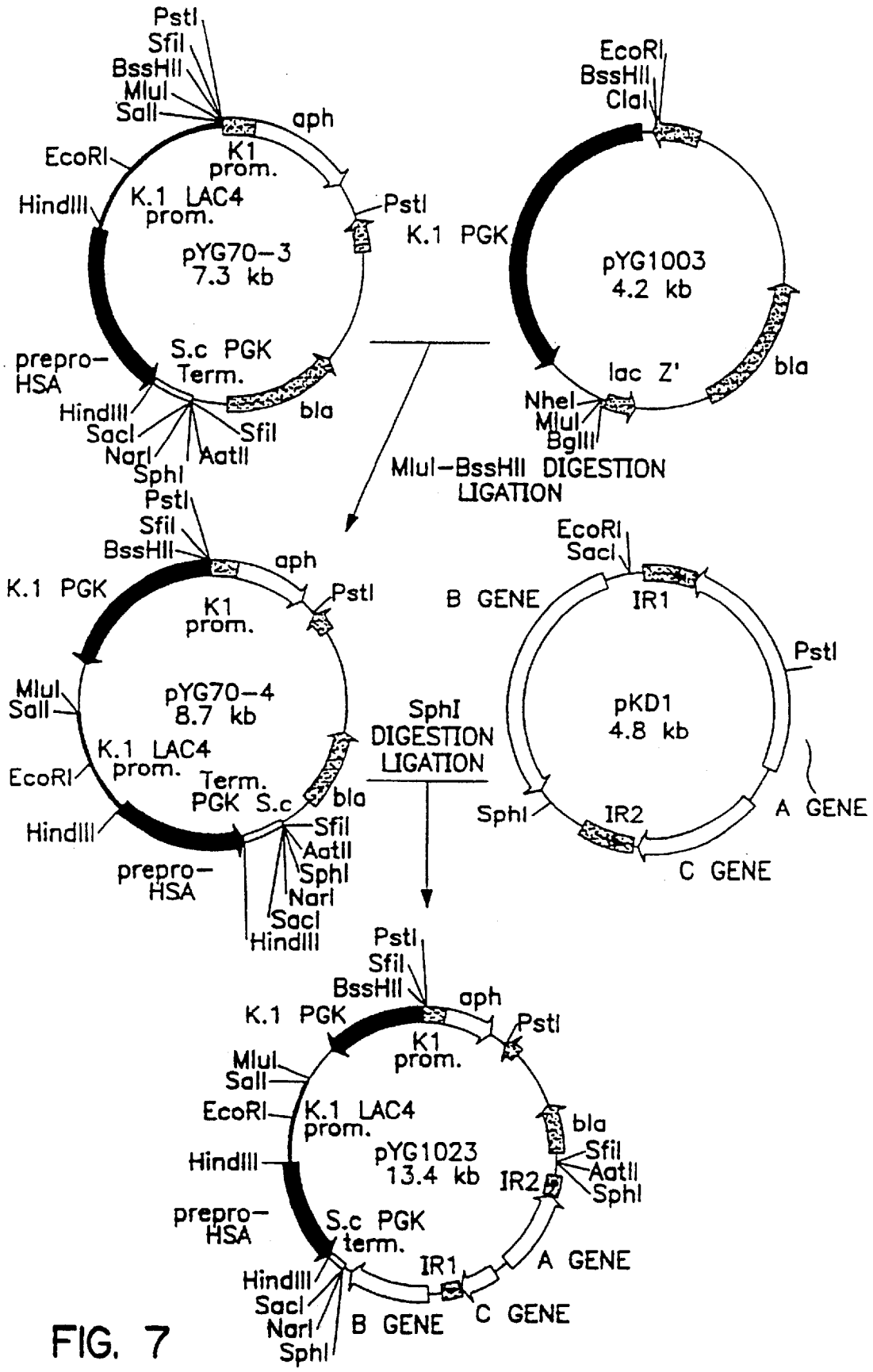

FIG. 7: Strategy for constructing the plasmid pYG1023. See FIG. 2 for the legend.

Figure 8:
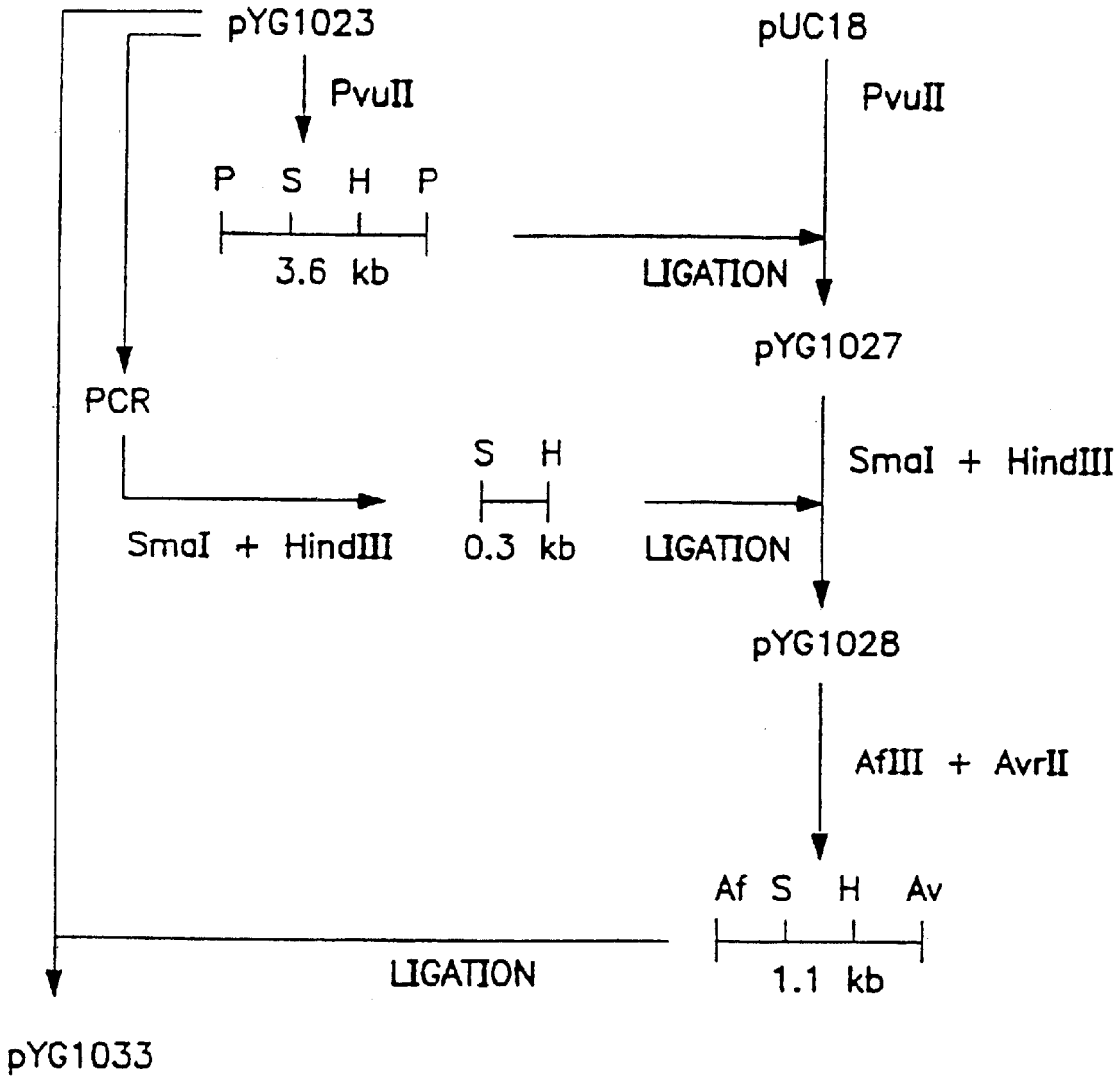

FIG. 8: Strategy for constructing the plasmid pYG1033. S=SmaI, H=HindIII, P=PvuII, Af=AflII, Av=AvrII.

FIG. 9: Representation of the vectors pYG1033 and pYG1033ΔSfiI. See FIG. 2 for the legend.

Figure 10:
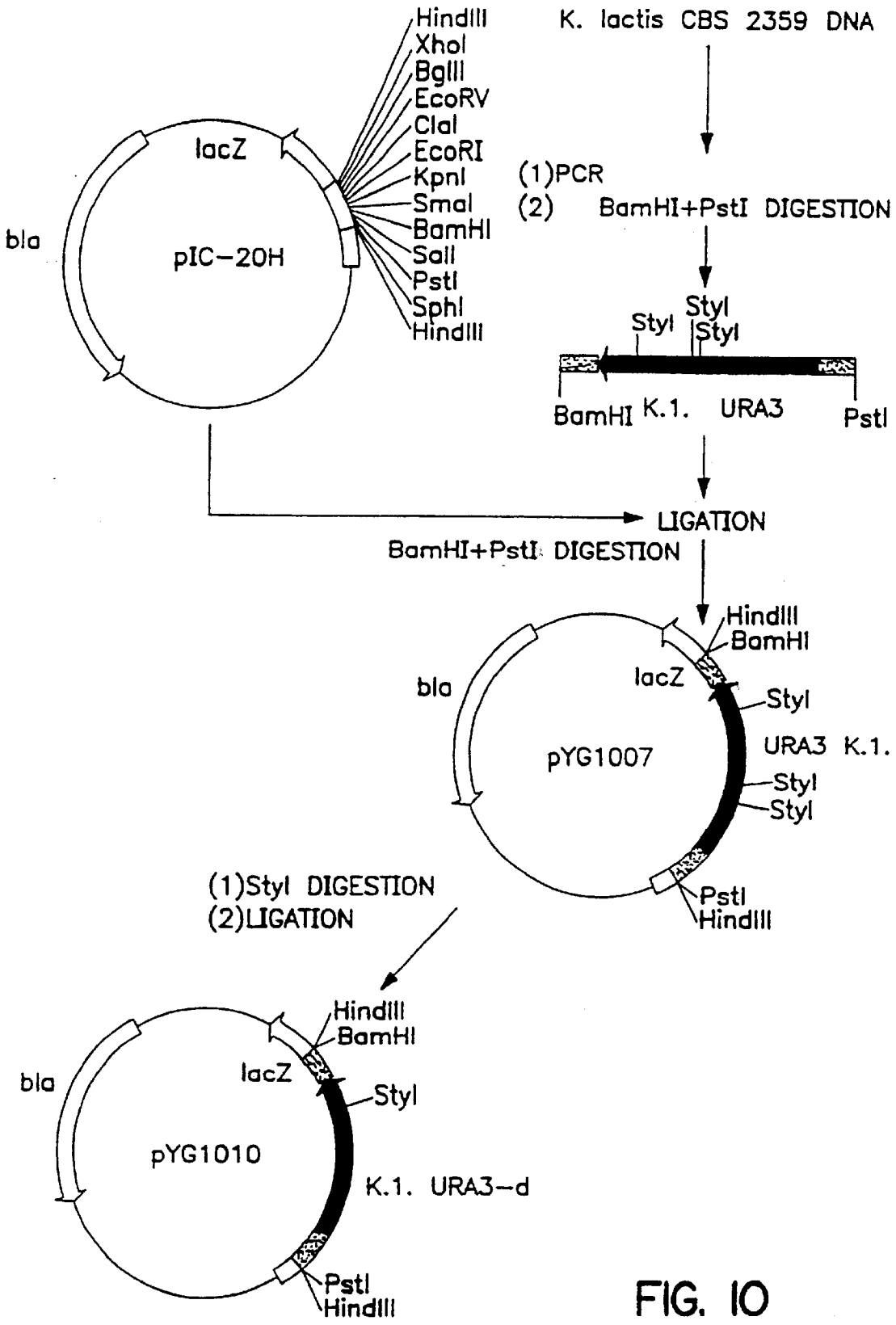

FIG. 10: Strategy for cloning and modifying the URA3 gene of K. lactis CBS2359.

Figure 11:
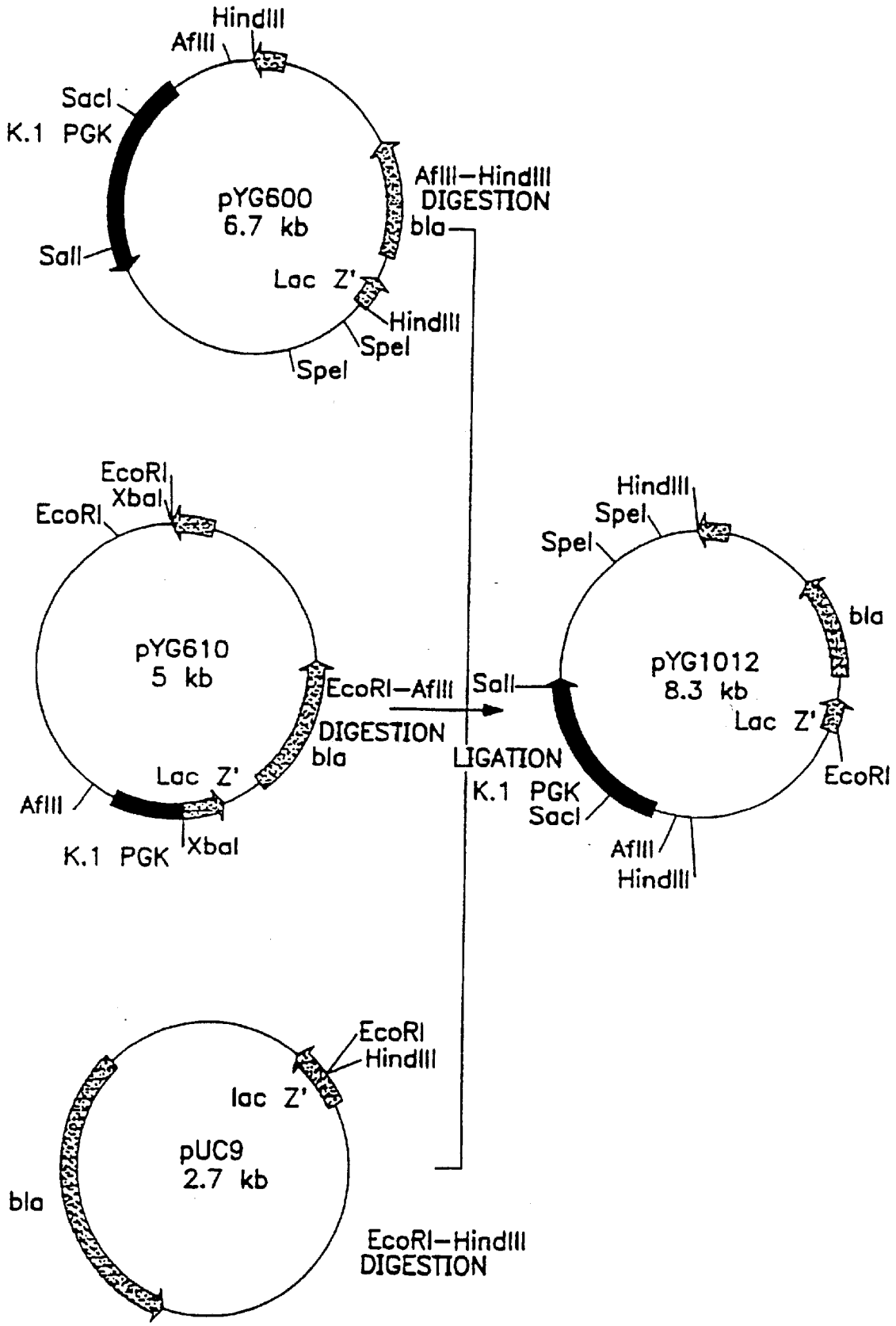

FIG. 11: Strategy for constructing the plasmid pYG1012.

Figure 12:
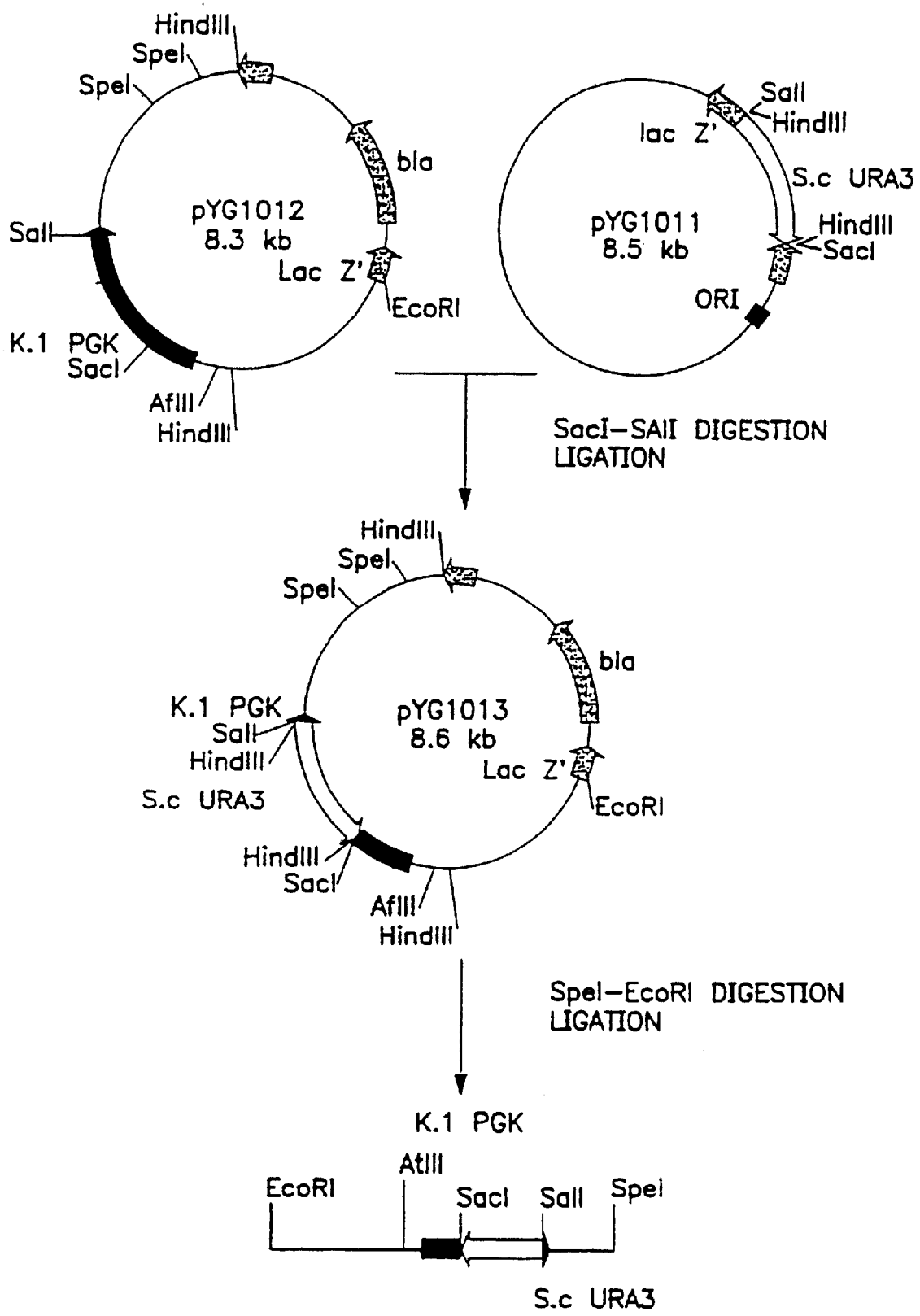

FIG. 12: Strategy for constructing the plasmid pYG1013. and representation of the EcoRI-SpeI fragment carrying the modified PGK K. 1 gene.

Figure 13:
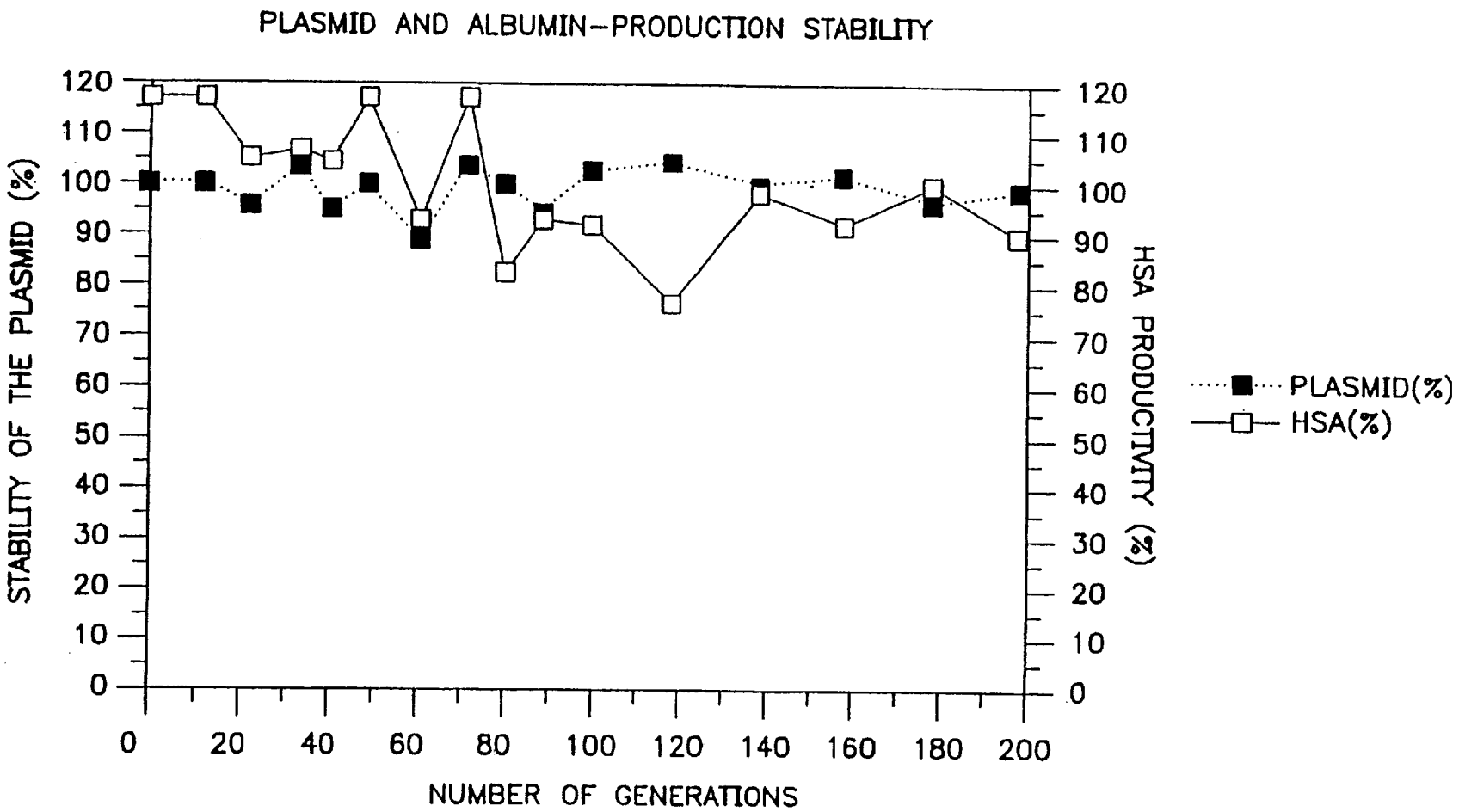

FIG. 13: This figure represents the production of human albumin by the plasmid pYG1023-transformed yeast FB05D, over 200 culture generations in an industrial-type complex medium, together with the stability of the plasmid pYG1023 in this yeast during the same period. The stability and the production of albumin are defined in the corresponding examples.

GENERAL CLONING TECHNIQUES

Conventional molecular biology methods such as centrifugation of plasmid DNA in a caesium chloride-ethidium bromide gradient, digestion with restriction enzymes, gel electrophoresis, electroelution of DNA fragments from agarose gels, transformation in E. coli and the like are described in the literature (Maniatis et al., "Molecular Cloning: a Laboratory Manual", Cold Spring Harbor Laboratory, Cold Spring Harbor, N.Y., 1986; Ausubel et al., (eds.), "Current Protocols in Molecular Biology", John Wiley & Sons, New York 1987).

Site-directed mutagenesis in vitro with oligodeoxynucleotides is carried out according to the method developed by Taylor et al. (Nucleic Acids Res. 13 (1985) 8749–8764) using the kit distributed by Amersham. The sequencing of nucleotides is performed according to the dideoxy technique described by Sanger et al, (Proc. Natl. Acad. Sci. USA, 74 (1977) 5463–5467). The enzymatic amplification of specific DNA fragments is carried out by the PCR reaction ("Polymerase Chain Reaction") under the conditions described by Mullis and Faloona (Meth. Enzym., 155 (1987) 335–350) and Saiki et al. (Science 230 (1985) 1350–1354) using a DNA thermal cycler (Perking Elmer Cetus) in accordance with the recommendations of the manufacturer.

EXAMPLES

Use of the K. lactis PGK Gene as Selection Marker

These examples describe the production of a host/vector pair in which the gene enabling the stability of the multiple copy plasmid to be increased is the gene which encodes K. lactis 3-phosphoglycerate kinase (PGK).

The pair thus obtained is stable in an industrial-type complex medium such as defined above.

EXAMPLE 1

Isolation of the K. lactis PGK Gene

The PGK gene was isolated from K. lactis CBS2359 by screening a partial genomic library with a heterologous probe corresponding to the N-terminal portion of the S. cerevisiae PGK gene (Dobson et al., Nucl. Acid. Res. 10 (1982) 2625–2637). More specifically, the probe used corresponds to the 1.3-kb PvuI-EcoRI fragment.

In Southern blot analysis (Southern et al., J. Biol. Chem. 98 (1975) 503), the probe used hybridises to a DNA sequence present on a 4-kb HindIII-HindIII fragment. This sequence was isolated by colony hybridisation using the above probe. For that, a limited genomic DNA library of the CBS2359 strain, consisting of HindIII fragments of between 3 and 5 kb in size introduced at the HindIII site of the plasmid pUC18, was prepared and screened.

A clone carrying the plasmid pYG600 (FIG. 1) was thus isolated. The sequence of the PGK gene carried by this plasmid has been described by Fournier et al. (Nucl. Acid. Res. 18 (1990) 369).

EXAMPLE 2

Construction of Expression Vectors for a Recombinant Protein, Carrying the K. lactis PGK Gene 2.1. Construction of the plasmid pYG70 (FIG. 2).

The plasmid pYG70 is derived from the plasmid pKan707 (see EP 361 991) by removal of EcoRI fragments containing the URA3 gene and the sequence of the pKD1 plasmid, and of the unique HindIII site present in the aph gene, so as to facilitate subsequent cloning steps. The aph gene encodes aminoglycoside 3'-phosphotransferase (I) (Oka et al., J. Mol. Biol. 147 (1981) 217), and is used as marker for geneticin (G418) resistance in yeast. The PstI fragment of the plasmid pKan707 containing the aph gene was subcloned into the bacteriophage M13mp7. The HindIII site present in this gene was then destroyed by site-directed mutagenesis according to the method described by Taylor et al. (cf. general cloning techniques), in order to generate the plasmid pYG65 (see FIG. 2). The following oligodeoxynucleotide was used to perform this mutagenesis:

5'-GAA ATG CAT AAG CTC TTG CCA TTC TCA CCG-3' (SEQ ID NO: 9)

This oligodeoxynucleotide enabled the triplet CTT which encodes leucine 185 to be replaced by CTC. This change does not modify the resulting protein sequence. To obtain the plasmid pYG70, the portion containing the bacterial replicon from pKan707 was isolated by digestion with the EcoRI enzyme and recircularised with T4 DNA ligase to form the plasmid pYG69 (FIG. 2). The PstI fragment present in the latter, containing the aph gene, was then replaced with the equivalent mutated fragment derived from the pYG65.

The plasmid pYG70 thus obtained therefore contains:

a replicon and a selection marker (bla gene which confers resistance to ampicillin) for E. coli, a selection marker for yeast (mutated aph gene) under the control of the killer toxin promoter k1.

2.2. Modification of the restriction sites of the plasmid pYG70 (FIG. 3).

To facilitate subsequent cloning steps, some restriction sites were removed (i) and 2 adaptors were added (ii and iii) to the plasmid pYG70.

(i) Removal of the SphI site.

The plasmid pYG70 was digested with SphI and the cohesive ends were then removed by digestion in the presence of phage T4 DNA polymerase. After ligation in the presence of ligase, the plasmid pYG70ΔSphI was obtained (see FIG. 3).

(ii) Insertion of the adaptor 1.

The adaptor 1 was obtained by hybridisation of the synthetic oligodeoxynucleotides A and B (SEQ ID NOS: 1 and 2) presented in FIG. 4. For that, 2 $\mu$g of each oligodeoxynucleotide were incubated in a 20 $\mu$l of hybridisation buffer (30 mM Tris-HCl buffer, pH 7.5; 30 mM NaCl; 7.5 mM $MgCl_2$; 0.25 mM ATP; 2 mM DDT; 0.2 mM EDTA), and then the temperature was raised to 80° C. for 10 minutes, and slowly reduced to room temperature.

The adaptor thus obtained contains cleavage sites for the following enzymes: SacI, SalI, MluI, BssHII and SfiI, and enables the SalI site present in the plasmid pYG70ΔSphI to be removed during its introduction. This adaptor was introduced by ligation into the plasmid pYG70ΔSphI, previously digested with the enzymes SalI and SacI.

The plasmid obtained is called pYG70-1.

(iii) Insertion of the adaptor 2.

The adaptor 2 was produced by following the procedure described for the adaptor 1, using the oligodeoxynucleotides C and D (SEQ ID NOS: 3 and 4) described in FIG. 4. This adaptor contains cleavage sites for the following enzymes: SfiI; AatII, SphI; NarI and SacI and enables the EcoRI site present in the plasmid pYG70-1 to be removed during its introduction. It was introduced by ligation into the plasmid pYG70-1, previously digested with the enzymes EcoRI and SacI, to form the plasmid pYG70-2 (FIG. 3).

2.3. Introduction of a human serum albumin expression cassette.

The human serum albumin expression cassette used comprises:

the inducible promoter of the K. lactis LAC4 gene the structural gene encoding human serum albumin (prepro form), and the terminator for the S. cerevisiae PGK gene.

This cassette was isolated from the plasmid pYG404 (EP 361 991 incorporated herein by reference) in the form of a SalI-SacI fragment and then introduced by ligation into the plasmid pYG70-2 previously digested with the corresponding enzymes.

The plasmid obtained is called pYG70-3 (FIG. 5).

2.4. Insertion of the K. lactis PGK gene.

The K. lactis PGK gene was isolated from the plasmid pYG600 (FIG. 1), subcloned into the plasmid pYG1002 in order to generate the plasmid pYG1003, and then isolated from the latter in the form of a MluI-BssHII fragment.

The subcloning into pYG1002 enabled the K. lactis PGK gene to be obtained free of its promoter and in the form of an MluI-BssHII fragment.

The plasmid pYG1003 was obtained in the following manner (FIG. 6):

The plasmid pIC20H (Marsh et al., Gene 32 (1984) 481) was digested with BglII and EcoRI so as to introduce the adaptor 3. This adaptor, which provides the EcoRI, BssHII, ClaI, NheI, MluI and BglII sites, was obtained as described above (2.2.(ii)), by hybridisation of the oligodeoxynucleotides E and F (SEQ ID NOS: 5 and 6; FIG. 4). The resulting plasmid is called pYG1002. The K. lactis PGK gene was introduced into this new plasmid in the form of a ClaI-NheI fragment derived from the plasmid pYG600. The plasmid obtained is called pYG1003 (FIG. 6).

The MluI-BssHII fragment derived from the plasmid pYG1003 carrying the K. lactis PGK gene was then introduced into the corresponding sites on the plasmid pYG70-3 in order to generate the plasmid pYG70-4 (FIG. 7).

On this plasmid, the K. lactis PGK gene is thereafter placed under the control of the killer toxin bidirectional promoter k1.

2.5. Insertion of the yeast replicon.

The plasmids pYG70-4 (FIG. 7) and pKD1 (EP 361 991) were digested with SphI and ligated together in the presence of ligase. After this ligation, 4 vectors may be obtained depending on the conformation of the plasmid pKD1 (A form or B form) and the orientation of the portion corresponding to the plasmid pYG70-4 relative to pKD1.

One of these constructs was selected and called pYG1023 (FIG. 7). This vector comprises:

the entire sequence of the plasmid pKD1, which makes pYG1023 a multiple copy plasmid which is stable and capable of replicating in yeasts and preferably yeasts of the Kluyveromyces genus, a human serum albumin expression cassette containing the structural gene which encodes the prepro form under the control of the inducible promoter of the K. lactis LAC4 gene, and of the terminator of the S. cerevisiae PGK gene, a replicon and a selection marker (bla gene_which confers resistance to ampicillin) for E. coli, two selection markers for the K. lactis strain FB05D (cf. Example 3): the mutated aph gene under the control of the killer toxin bidirectional promoter k1 and the K. lactis PGK gene under the control of the same promoter but divergently transcribed relative to the aph gene.

2.6. Construction of the vector pYG1033ΔSfiI.

A construct derived from the plasmid pYG1023 was produced with the aim of obtaining, on introduction into yeast, expression vectors free of bacterial replicon and markers for resistance to ampicillin and to geneticin, and in which the k1 promoter situated upstream of the PGK gene is removed. This construct was produced in the following manner:

(i) Modification of the PGK terminator.

This step is optional. However, it was carried out so as to avoid any risk of recombination within the expression vector itself, which would lead to a reduction in the host/vector pair-producing capacities. Indeed, the fragment used as terminator inside the plasmid pYG1023 contains the S. cerevisiae PGK terminator and also the C-terminal portion of the S. cerevisiae PGK structural gene and, as a result, exhibits a homology with the corresponding region of the K. lactis PGK gene used as selection marker. This terminator was therefore modified in the following manner:

The 3.6-kb PvuII fragment isolated from pYG1023 was, in the first instance, subcloned into the corresponding sites of the vector pUC18 to form the plasmid pYG1027. The 427-bp SmaI-HindIII fragment of this plasmid, carrying the PGK terminator region, was then replaced with a 325-bp fragment corresponding to the noncoding 3' region of the S. cerevisiae PGK gene (that is to say containing no element of the structural gene). This 325-pb fragment was obtained by PCR amplification reaction (cf. general cloning techniques) on the PGK terminator present in the plasmid pYG1023, by using the following oligodeoxynucleotides:

```
5'-GGAAAGCTTCGGACCGTAAATTGAAT-
   TGAATTGAAATC-3' (SEQ ID NO: 10)

5'-CCATCCCGGGAGCTCATCCGAATTAATTCCCAGC-3'
   (SEQ ID NO: 11)
```

and then digested with the enzymes SmaI and HindIII. The vector obtained was designated pYG1028 (FIG. 8). Digestion of the latter with the enzymes AvrII and AflII enables a 1.1-kb fragment to be isolated, which was used to replace the corresponding fragment in pYG1023. The plasmid obtained was designated pYG1033 (FIG. 9).

(ii) Deletion of the SfiI fragment.

The plasmid pYG1033 was then subjected to digestion in the presence of the enzyme SfiI in order to excise the 3.5-kb fragment containing the bacterial replicon and the resistance markers, and then to ligation in the presence of ligase so as to generate the plasmid pYG1033ΔSfiI (FIG. 9).

EXAMPLE 3

Isolation of a K. lactis pgk Mutant

This example described the preparation of a pgk mutant from a wild K. lactis strain by avoiding the use of genes for resistance to antibiotics. Two steps were carried out successively:

(i) preparation of a ura3 auxotrophic strain (Example 3.1.), and (ii) replacement of the PGK gene (replacement gene, Rothstein, mentioned above) with a DNA fragment carrying the PGK gene modified by substitution of an inner portion of the gene by a DNA fragment carrying the S. cerevisiae URA3 gene. The pgk mutant was thus prepared by directed removal of nearly the entire open reading frame (ORF) of the PGK gene in the genome of the ura3 strain (cf. Example 3.2.).

This mutagenesis technique makes it possible to avoid the use of nonspecific mutagenic agents which may affect other regions of the cell genome. It also makes it possible to avoid any genetic reversion event which carries the risk of correcting the modifications carried out on the PGK gene.

3.1. Construction of a K. lactis ura3 mutant.

(i) Cloning and modification of the K. lactis CBS2359 URA3 gene (FIG. 10).

The K. lactis URA3 gene which encodes orotidine-5-phosphate decarboxylase (Shuster et al., Nucl. Acid. Res. 15 (1987) 8573) was cloned in the form of a 1.2-kb BamHI-PstI fragment using the PCR technique (cf. general cloning techniques), starting with a K. lactis CBS2359 genomic DNA extract (Rose et al., "Methods in Yeast Genetics" Cold Spring Harbor Laboratory Press, N.Y., 1990), by means of the following oligodeoxynucleotides:

```
5'-GGAAGCTTGGCTGCAGGAATTGTCGT-
   TCATGGTGACAC-3' (SEQ ID NO: 12)

and

5'-CCGAATTCCCGGATCCCATAATGAAA-
   GAGAGAGAGAGAAGCAAAC-3' (SEQ ID NO: 13)
```

The fragment obtained was then subcloned into the BamHI and PstI sites of the plasmid pIC20H to give the plasmid pYG1007 (FIG. 10). The URA3 gene was then modified by deletion of a StyI fragment inside ORF, comprising 286 bp. This was carried out on pYG1007 by digestion with the enzyme StyI followed by ligation in the presence of ligase. This new plasmid is called pYG1010 (FIG. 10).

(ii) Transformation of K. lactis CBS293.91 by the deleted URA3 gene.

The CBS 293.91 strain was transformed according to the procedure described by Durrens et al. (Curr. Genet. 18 (1990) 7) with 10 μg of the PstI-BamHI fragment isolated by electroelution from the plasmid pYG1010, which contains the deleted URA3 gene. After a sudden rise in temperature to 42° C. (heat shock) and 2 successive washes with water, 600 μl of YPD medium (10 g/l yeast extract; 20 g/l peptone; 20 g/l glucose) were added and the cells were incubated overnight. The cells were then plated on an SD minimal synthetic medium (6.7 g bacto-yeast nitrogen base without amino acids (Difco); 20 g glucose; 20 g Bacto-agar; 1000 ml distilled water) in the presence of uracil (100 μg/ml), of uridine (100 μg/ml) and 5-fluoroorotate (5FO) 15 mM. Clones appeared after 4 to 5 days. They were subcultured on YPD medium so as to obtain isolated colonies.

From the 1st subculture, 3 clones derived from the colony which initially appeared on the SD+5FO medium were reisolated on YPD medium (secondary subculture).

The clones derived from the secondary subculture were then tested for the Ura3⁻ phenotype using a drop test on SD and SD+uracil medium (Jund and Lacroute, J. of Bact. 102 (1970) 607–615; Bach and Lacroute, Mol. Gen. Genet. 115 (1972) 126–130). The ura3 phenotype of the clones obtained was checked by:

PCR reaction using the oligodeoxynucleotides described for the cloning in 4.1., which enables the clones carrying the deleted or intact URA3 gene to be identified by a difference in the size of the amplification (0.9 and 1.2 kb, respectively);

complementation by means of the plasmid pKan707 (EP 361 991) carrying the intact S. cerevisiae URA3 gene, which is known for its capacity to complement the ura3 mutation in K. lactis (De Louvencourt, mentioned above); and Southern blot on the genomic DNA of the identified clones using as probe the K. lactis URA 3 gene isolated in Example 3.1. labelled with $^{32}$p according to the technique described by Feinberg and Vogelstein (Anal.

Biochem. 132 (1983) 6). This step enables the clones carrying the deleted or intact URA3 gene to be identified by the difference in the size of the fragment revealed by hybridisation.

The ura3. mutant selected is called K. lactis Y616.

3.2. Construction of a K. lactis Y616 pgk mutant.

A DNA fragment was prepared containing a PGK gene modified by substitution of an inner portion of a gene with a DNA fragment carrying the S. cerevisiae URA3 gene. This fragment was then used to replace the intact genomic copy of the PGK gene by double homologous recombination (Rothstein, mentioned above).

(i) Construction of a DNA fragment containing the modified PGK-gene (FIGS. 11 and 12).

In order to increase the frequency of homologous recombination, the PGK gene was restored, in the first instance, delimited by larger flanking regions. In particular, the regions situated upstream of the PGK gene were cloned and then ligated into the fragment carrying the plasmid pYG600 (FIG. 1).

Cloning of the region upstream of the PGK gene.

Screening of the library described in Example 1 also enabled on XbaI genomic fragment of about 2.5 kb to be revealed by Southern blot analysis. This fragment was isolated by screening a limited K. lactis CBS2359 genomic library consisting of XbaI-cut DNA fragments of between 2 and 3 kb is size, which were introduced into the XbaI site of the plasmid pUC18. A library with 500 clones was thus prepared and then screened with the heterologous probe used in Example 1. A clone was identified by colony hybridisation and its plasmid DNA isolated. This plasmid, pYG610 (FIG. 11), contains a 2.5-kb genomic DNA fragment. Analysis of the sequence of this fragment shows that it contains a portion which encodes the N-terminal region of the K. lactis Pgk protein (0.3 kb), and 2.2 kb corresponding to the region situated upstream of the PGK gene.

Construction of the plasmid pYG1012 (FIG. 11).

The AflII-HindIII fragment of plasmid pYG600 and EcoRI-AflII fragment of the plasmid pYG610 were isolated by electroelution and then introduced together, by ligation, into the plasmid pUC9 previously digested with EcoRI and Hind III. The plasmid obtained is called pYG1012.

Modification of the PGK gene.

The SalI-SacI fragment inside the PGK gene, which is carried by the plasmid pYG1012, was replaced by digestion followed by ligation with the SalI-SacI fragment derived from the plasmid pYG1011, carrying the S. cerevisiae URA3 gene, in order to generate the plasmid pYG1013 (FIG. 12).

The plasmid pYG1011 was constructed by insertion of a HindIII fragment isolated from the plasmid YEp24 (ATCC No. 37051), containing the S. cerevisial URA3 gene, into the corresponding sites of the bacteriophage M13tg130 (Kieny et al., Gene 26 (1983) 101).

The plasmid pYG1013 therefore contains, in the form of an EcoRI-SpeI fragments, the S. cerevisiae URA3 gene, delimited on one side of the noncoding 5' region of the first 500 pairs of the K. lactis PGK structural gene, and on the other by the last 100 base pairs of the K. lactis PGK structural gene and its terminator (FIG. 12).

(ii) Transformation of K. lactis Y616 by the modified PGK gene.

The Y616 strain (ura3) was transformed according to the method described by Durrens et al. (mentioned above), with 10 $\mu$g of the EcoRI-SpeI fragment isolated from the plasmid pYG1013.

After transformation, the cells containing the functional URA3 gene were selected on an SD minimal synthetic medium in which glucose was replaced by glycerol (3%) and ethanol (2%). This medium permits the growth of the pgk mutants.

The transformed colonies thus obtained were then subcultured in a complex YPD medium in which the pgk mutants are unable to grow. 50% of the strains obtained exhibited a $Pgk^-$ phenotype in this test.

Mutation in the PGK, gene was checked in the colonies thus identified by the PCR amplification reaction using the oligodeoxynucleotides G and H (SEQ ID NOS: 7 and 8) described in FIG. 4. These 2 oligodeoxynucleotides make it possible to amplify:

a region of about 0.9 kb in the intact K. lactis PGK gene, and a region of about 1.3 kb in the K. lactis PGK gene modified as described above (i).

The amplification was carried out on whole cells exhibiting the $Pgk^-$ phenotype. After 30 amplification cycles, the supernatants (10 $\mu$l) were analyzed on agarose gel (0.8%) electrophoresis in order to determine the size of the bands. The controls were produced by amplification using the same oligodeoxynucleotides on the plasmids pYG600 (intact gene) and pYG1013 (modified gene).

The results obtained show that a 1.3-kb band is amplified in the $Pgk^-$ strains. These strains therefore effectively possess a modified PGK gene. Among them, a pgk mutant was selected and called K. lactis FB05D.

EXAMPLE 4

Transformation of the K. lactis Strain FB05D by the Plasmids pYG1023 and pYG1033ΔSfiI The vector pYG1023 was introduced, by transformation, into the K. lactis strain FB05D, using an ethylene glycol/dimethyl sulphoxide technique (Durrens et al., mentioned above). Transformed yeasts were selected for the $Pgk^+$ phenotype conferred by the plasmid pYG1023 on a complex YPD medium.

The vector pYG1033ΔSfiI was introduced into a K. lactis strain FB05D by electroporation according to the technique described by Meilhoc et al. (Biotechnologie 8 (1990) 223). After transformation, the cells were plated on YPD medium and cultured at 30° C. for 3 days. The cells which are capable of growing on this type of medium (therefore containing a functional copy of the PGK gene) were then tested for their resistance to geneticin. 60% of them are unable to grow on YPD medium in the presence of 200 $\mu$g/ml of G418. These results show that the introduced vector has lost the G418 marker and that it is capable of complementing the pgk mutation of the FB05D strain.

EXAMPLE 5

Study of the Stability of the Plasmid pYG1023 and the Production of Albumin 5.1 Stability study The transformed cells were precultured in Erlenmeyer flasks in an M9CS20 industrial-type complex medium [M9 medium (Maniatis et al., mentioned above) supplemented with 20 g/l of maize soluble extract (Solulys. L, Roquette) in the presence of 2 g/l of ammonium acetate and 20 g/l of lactose] at 28° C. with stirring.

This procedure was then used to inoculate two 300-ml Erlenmeyer flasks containing 50 ml of M9CS20 medium, at a dilution of $10^{-3}$ (Erlenmeyer flask 1) and $10^{-6}$ (Erlenmeyer flask 2). The cells were then cultured as above, for 3 days, with stirring (200 revolutions/min). At this stage, the cells in Erlenmeyer flask 1 has undergone 10 cellular divisions (10 generation times), and the cells in Erlenmeyer flask 2 had undergone 20 cellular divisions (20 generation times).

The culture in Erlenmeyer flask 2 was then used in its turn to inoculate two other Erlenmeyer flasks at a dilution of $10^{-3}$ (Erlenmeyer flask 3) and $10^{-6}$ (Erlenmeyer flask 4). The cells were then cultured as above, for 3 days. At this stage, the cells in Erlenmeyer flask 3 had undergone 30 cellular divisions (30 generation times), and the cells in Erlenmeyer flask 4 had undergone 40 cellular divisions (40 generation times).

This operation was again repeated 8 times so as to obtain Erlenmeyer flask 5–20 containing cultures having undergone from 50 up to 200 cellular divisions.

At the end of each culture, a sample was collected from the Erlenmeyer flask so as to prepare a suspension containing $10^3$ cells/ml. 200 $\mu$l of these suspensions were then plated on 2 types of dishes:

YPGE dish (10 g/l yeast extract, 20 g/l peptone, 30 g/l glycerol, 20 g/l ethanol). This medium permits the growth of all the cells.

YPD dish in the presence of G418 (200 $\mu$g/ml). Only the cells containing the plasmid pYG1023 which carries the gene for resistance to G418 and the PGK gene are capable of growing on this type of dish.

The stability of the plasmid pYG1023 was thus determined for each culture. The results are presented in FIG. 13, in which the stability is defined by the ratio of the number of colonies present on the YPD/G418 dishes to the number of colonies present on the YPGE dishes.

The results demonstrate the adavantages of the invention relative to the prior art. Indeed, although pKD1-based stable plasmids have already been described, the introduction of expression cassettes into them, permitting the production of recombinant proteins, is always accompanied by a decrease in stability. This was observed in particular for albumin and interleukin-1β (EP 361 991). The present invention enables this loss of stability to be eliminated since, under conditions for inducing the expression (lactose), the vectors are maintained in 100% of the transformed cells after 200 generations of culture.

5.2. Study of albumin production

At the end of each culture, obtained according to the procedure described in 5.1., 10 $\mu$l of supernatant free of cells were collected from each Erlenmeyer flask and mixed with an equivalent volume of 2×Laemmli buffer (Laemmli, Nature 227 (1970) 680). After heating at 96° C. for 10 minutes, the proteins in the sample were separated on 8.5% SDS-polyacrylamide gel. The production of albumin was then revealed by staining gel with Coomassie blue, and evaluated by densitometry using a Shimazu CS930 densitometer (the margin of error of this technique is: +/−20%). FIG. 13 shows the variation of albumin production as the function of the number of culture generations under conditions for induction (medium containing lactose). The values are given in percentage of production relating to the mean production measured over 200 generations.

These results confirm the high stability of a host/vector pair described and its capacity to produce, at constant and high levels, under conditions for induction, a recombinant protein over 200 culture generations, at least in an industrial-type complex medium.

One skilled in the art will readily appreciate the present invention is well adapted to carry out the objects and obtain the ends and advantages mentioned, as well as those inherent therein. The DNA sequences, recombinant DNAs, vectors, cells, methods, procedures, and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

DEPOSIT OF STRAINS USEFUL IN PRACTICING THE INVENTION

A sample of K. lactis Y616 and K. lactis FB05D strains was deposited on Jun. 11, 1991 in Centraalbureau voor Schimmelkulturen (CBS) at Baarn in the Netherlands, in accordance with the conditions of the Budapest treaty under the numbers CBS 294.91 and CBS 295.91, respectively. The K. lactis strain CBS 293.91 corresponds to the strain CBS1065 redeposited on Jun. 11, 1991 in accordance with the conditions of the Budapest treaty.

SEQUENCE LISTING

```
(1) GENERAL INFORMATION:

   (iii) NUMBER OF SEQUENCES: 13


(2) INFORMATION FOR SEQ ID NO: 1:

     (i) SEQUENCE CHARACTERISTICS:
          (A) LENGTH: 37 base pairs
          (B) TYPE: nucleic acid
          (C) STRANDEDNESS: single
          (D) TOPOLOGY: linear

    (ii) MOLECULE TYPE: other nucleic acid

    (xi) SEQUENCE DESCRIPTION: SEQ ID NO: 1:

 CGTCGACACG CGTGCGCGCC CGCGGCCAAT GGGGCCC                    37


(2) INFORMATION FOR SEQ ID NO: 2:
```

-continued (i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 2:

TCGAGGGCCC CATTGGCCGC GGGCGCGCAC GCGTGTCGAC GAGCT 45

(2) INFORMATION FOR SEQ ID NO: 3:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 3:

AATTAGGCCA ATGGGGCCGA CGTCGCATGC GGCGCCGAGC T 41

(2) INFORMATION FOR SEQ ID NO: 4:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 4:

CGGCGCCGCA TGCGACGTCG GCCCCATTGG CCT 33

(2) INFORMATION FOR SEQ ID NO: 5:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 5:

AATTCCCCGC GCGCCCATCG ATCCGCTAGC CCACGCGTCC A 41

(2) INFORMATION FOR SEQ ID NO: 6:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 6:

GATCTGGACG CGTGGGCTAG CGGATCGATG GGCGCGCGGG G 41

(2) INFORMATION FOR SEQ ID NO: 7:

(i) SEQUENCE CHARACTERISTICS:
(A) LENGTH: 19 base pairs
(B) TYPE: nucleic acid

-continued (C) STRANDEDNESS: single
(D) TOPOLOGY: linear (ii) MOLECULE TYPE: other nucleic acid (xi) SEQUENCE DESCRIPTION: SEQ ID NO: 7:

TGCCTTCGGT ACCGCTCAC 19

(2) INFORMATION FOR SEQ ID NO: 8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 8:

AGAAGGGAAG GGATGATGGA 20

(2) INFORMATION FOR SEQ ID NO: 9:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 9:

GAAATGCATA AGCTCTTGCC ATTCTCACCG 30

(2) INFORMATION FOR SEQ ID NO: 10:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: other nucleic acid (xi) SEQUENCE DESCRIPTION: SEQ ID NO: 10:

GGAAAGCTTC GGACCGTAAA TTGAATTGAA TTGAAATC 38

(2) INFORMATION FOR SEQ ID NO: 11:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 11:

CCATCCCGGG AGCTCATCCG AATTAATTCC CAGC 34

(2) INFORMATION FOR SEQ ID NO: 12:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: other nucleic acid -continued

```
    (xi) SEQUENCE DESCRIPTION: SEQ ID NO: 12:

 GGAAGCTTGG CTGCAGGAAT TGTCGTTCAT GGTGACAC                          38


(2) INFORMATION FOR SEQ ID NO: 13:

     (i) SEQUENCE CHARACTERISTICS:
          (A) LENGTH: 45 base pairs
          (B) TYPE: nucleic acid
          (C) STRANDEDNESS: single
          (D) TOPOLOGY: linear

    (ii) MOLECULE TYPE: other nucleic acid

    (xi) SEQUENCE DESCRIPTION: SEQ ID NO: 13:

 CCGAATTCCC GGATCCCATA ATGAAAGAGA GAGAGAGAAG CAAAC                   45
```

We claim:

1. Yeast of the Kluyveromyces genus exhibiting the Pgk⁻ phenotype.

2. K. lactis yeast FB05D.

3. A host/vector pair which is stable in a complex medium, wherein the host is a yeast of the Kluyveromyces genus lacking a functional phosphoglycerate kinase gene, and wherein the vector comprises a functional copy of the phosphoglycerate kinase gene.

4. The host/vector pair according to claim 3, wherein the functional copy of the phosphoglycerate kinase gene present in the vector is placed under the control of a weak promoter or a defective promoter, or is completely free of a promoter.

5. The host/vector pair according to claim 3, wherein the host is selected from the group consisting of Kluyveromyces lactis and Kluyveromyces fragilis.

6. The host/vector pair according to claim 3, wherein the vector additionally comprises a DNA sequence encoding a desired protein, and signals permitting expression of said sequence.

7. The host/vector pair according to claim 6, wherein the protein is selected from the group consisting of enzymes, blood derivatives, insulin, variants of insulin, lymphokines, growth factors, apolipoproteins, antigenic polypeptides for the production of vaccines, viral receptors, and fusion polypeptides comprising an active part fused to a stabilising part.

8. The host/vector pair according to claim 7, wherein said enzymes are selected from the group consisting of superoxide dismutase, catalase, amylases, lipases, amidases, and chymosin.

9. The host/vector pair according to claim 7, wherein said blood derivatives are selected from the group consisting of serum albumin, variants of serum albumin, alpha-globin, beta-globin, factor VII, factor IX, non Willebrand factor (vWF), biologically active fragments of vWF, fibronectin and 1-alpha-antitrypsin.

10. The host/vector pair according to claim 7, wherein said lymphokines are selected from the group consisting of the interleukins, interferons, and colony stimulation factors.

11. The host/vector pair according to claim 7, wherein said colony stimulation factors are selected from the group consisting of G-CSF, GM-CSF, M-CSF, TNF, and TRF.

12. The host/vector pair according to claim 7, wherein said growth factors are selected from the group consisting of growth hormone, erythropoietin, FGF, EGF, PDGF, and TGF.

13. The host/vector pair according to claim 7, wherein said antigenic polypeptides are selected from the group consisting of antigens from a hepatitis virus, cytomegalovirus virus, an Epstein-Barr virus, and a herpes virus.

14. A method for producing proteins, said method comprising culturing the host/vector pair of claim 6 and recovering the proteins produced, wherein the protein is selected from the group consisting of enzymes, blood derivatives, insulin, variants of insulin, lymphokines, growth factors, apolipoproteins, antigenic polypeptides for the production of vaccines, viral receptors, and fusion polypeptides comprising an active part fused to a stabilising part.

15. The method according to claim 14, wherein said enzymes are selected from the group consisting of superoxide dismutase, catalase, amylases, lipases, amidases, and chymosin.

16. The method according to claim 14, wherein said blood derivatives are selected from the group consisting of serum albumin, variants of serum albumin, alpha-globin, beta-globin, factor VIII, factor IX, non Willebrand factor (vWF), biologically active fragments of vWF, fibronectin and 1-alpha-antitrypsin.

17. The method according to claim 14, wherein said lymphokines are selected from the group consisting of the interleukins, interferons, and colony stimulation factors.

18. The method according to claim 14, wherein said colony stimulation factors are selected from the group consisting of G-CSF, GM-CSF, M-CSF, TNF, and TRF.

19. The method according to claim 14, wherein said growth factors are selected from the group consisting of growth hormone, erythropoietin, FGF, EGF, PDGF, and TGF.

20. The method according to claim 14, wherein said antigenic polypeptides are selected from the group consisting of antigens from a hepatitis virus, a cytomegalovirus virus, an Epstein-Barr virus, and a herpes virus.

21. The host/vector pair according to claim 6 wherein the DNA sequence additionally comprises signals enabling secretion of the protein.

22. The host/vector pair according to claim 6 wherein the signals enabling the expression of the [second] DNA sequence are selected from the group consisting of transcription promoters and terminators.

23. The host/vector pair according to claim 22, wherein said promoters are selected from the group consisting of promoters of yeast genes, and modified promoters of yeast genes.

24. A method for producing a recombinant protein, comprising culturing the host/vector pair of claim 6 and recovering the protein produced.

25. The method according to claim [14 for producing]*16 wherein said blood derivatives are* human serum albumin, its precursors and variants.

26. An expression vector comprising a first DNA sequence encoding functional Kluyveromyces phosphoglycerate kinase, a second DNA sequence encoding a pharmaceutical protein, and a third DNA sequence encoding signals permitting expression of said second DNA sequence.

27. A vector selected from the group consisting of pYG1023, pYG1033 and pYG1033ΔSfiI.

* * * * *